Figure 1:
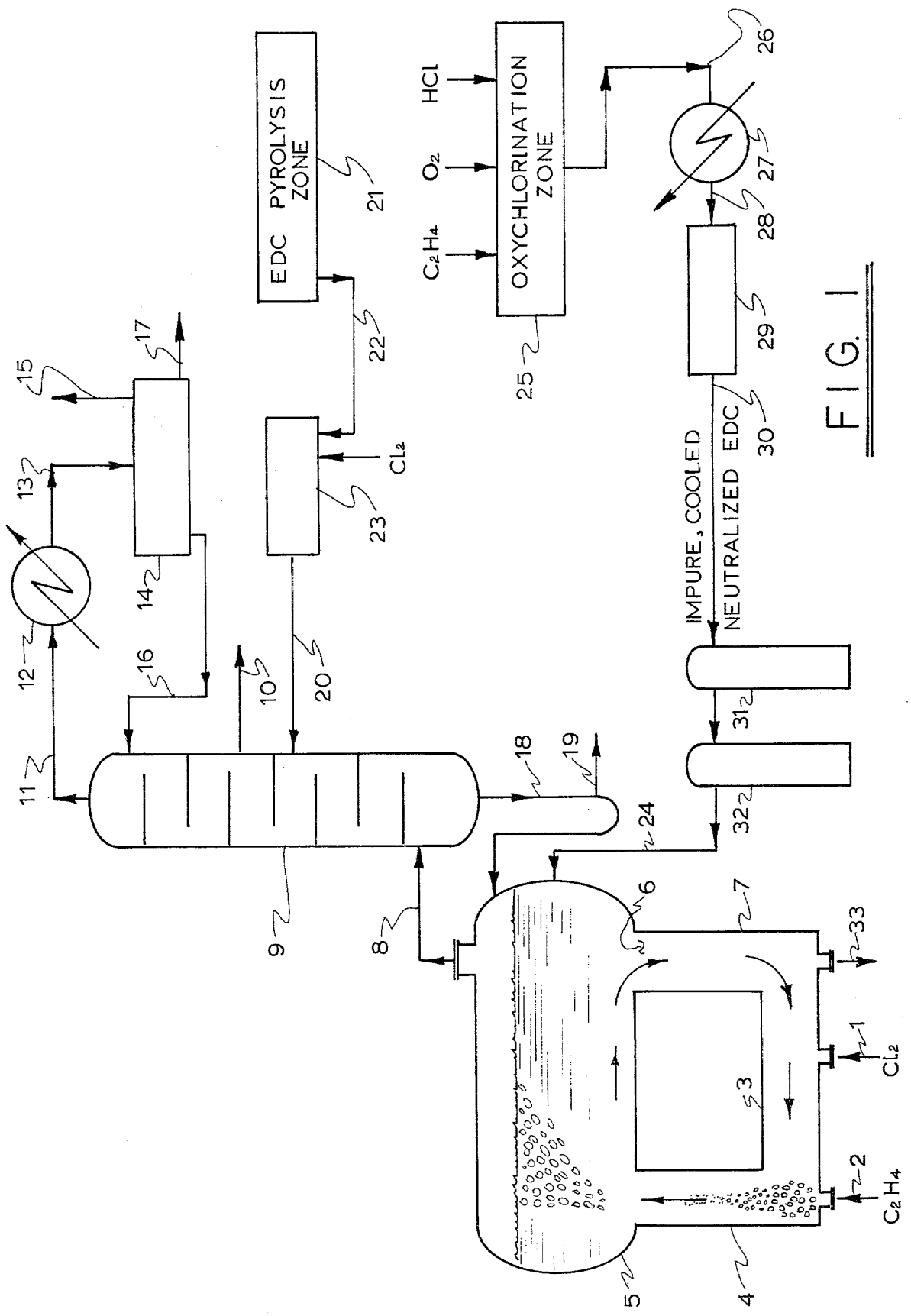
Figure 2:
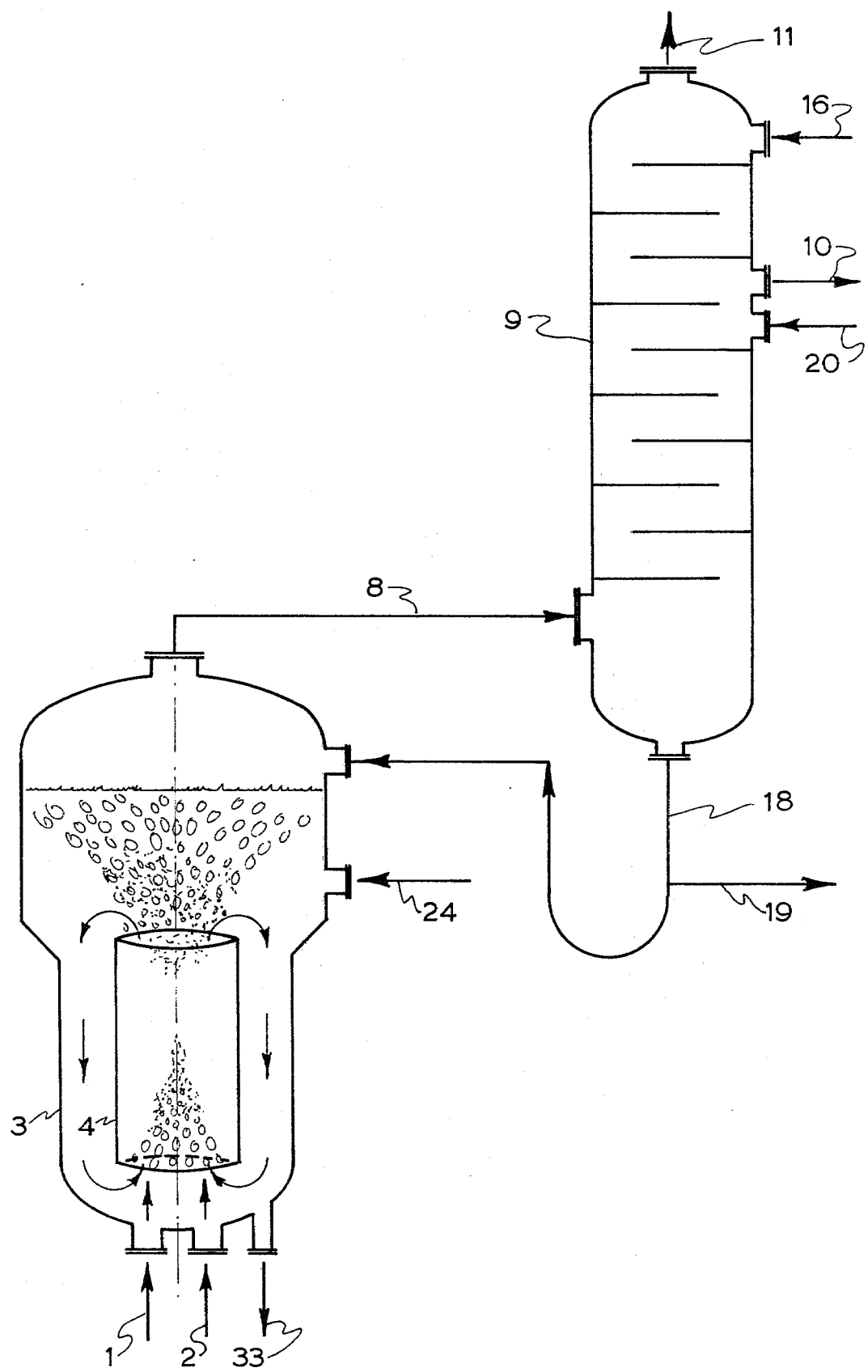
Figure 3:
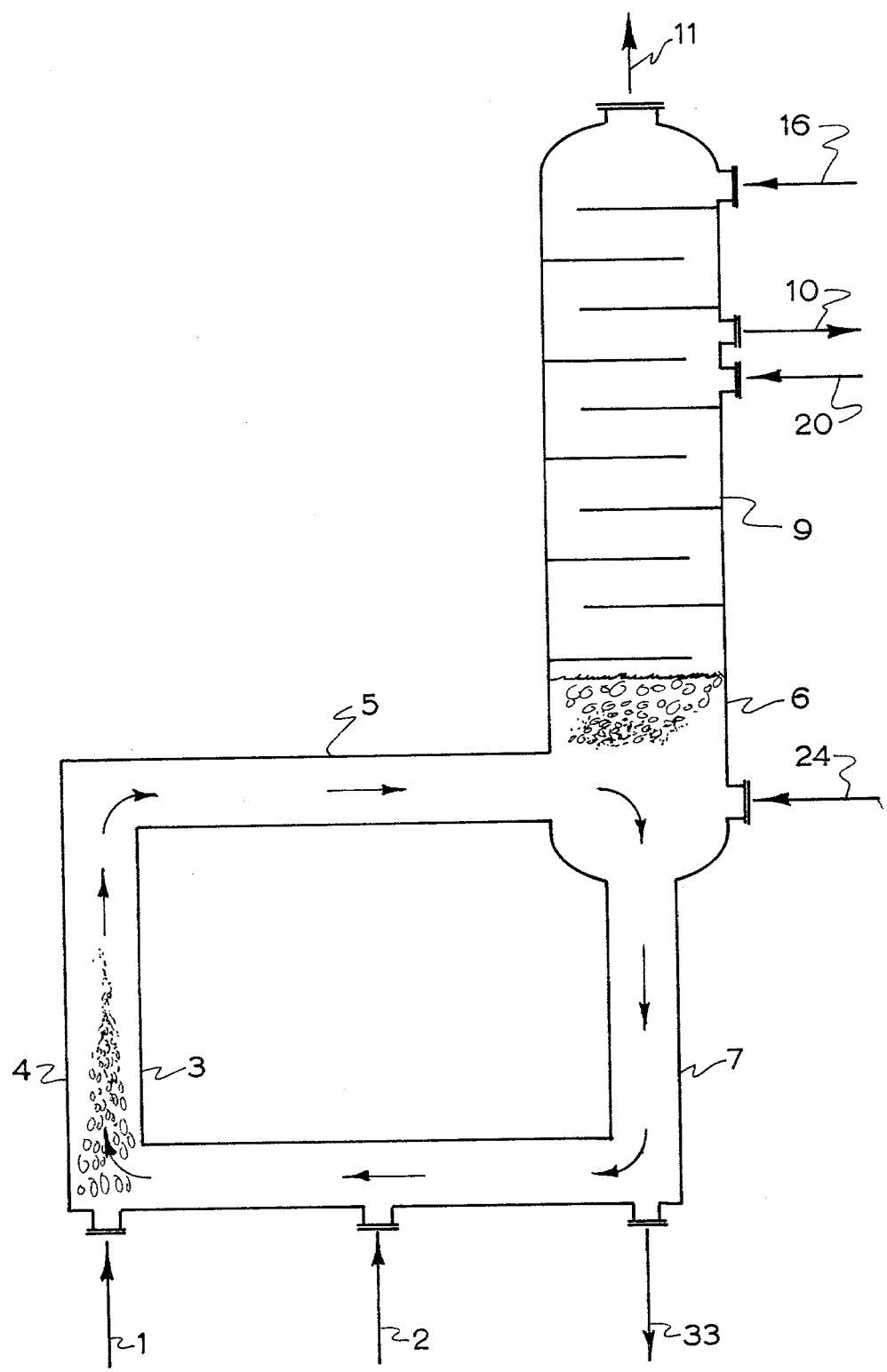

United States Patent [19]

Saito et al.

[11] 4,347,386
[45] Aug. 31, 1982

[54] PROCESS FOR PREPARING CYCLOPENTENOLONES

[75] Inventors: Kenji Saito, Toyonaka; Hiroshi Yamachika, Ibaraki, both of Japan

[73] Assignee: Sumitomo Chemical Company, Limited, Osaka, Japan

[21] Appl. No.: 256,570

[22] Filed: Apr. 22, 1981

[30] Foreign Application Priority Data

Apr. 30, 1980 [JP] Japan ................................. 55/58475
Nov. 20, 1980 [JP] Japan ................................. 55/164372

[51] Int. Cl.³ ............................................. C07C 45/67
[52] U.S. Cl. ..................................... 568/310; 568/341
[58] Field of Search ............................. 568/341, 310

[56] References Cited

U.S. PATENT DOCUMENTS

| 3,932,510 | 1/1976 | Muller | 568/341 |
| 3,932,511 | 1/1976 | Muller | 568/341 |
| 3,981,920 | 9/1976 | Buchi | 568/379 |
| 4,234,516 | 11/1980 | Koller et al. | 568/341 |

FOREIGN PATENT DOCUMENTS 53-21146 1/1978 Japan .
53-127462 9/1978 Japan .

OTHER PUBLICATIONS

J. Am. Chem. Soc., Stork et al., "A Route to Prostaglandins via a General Synthesis of 4-Hydroxycyclopentenones", 97, pp. 3258–3260, (1975).
Synthesis, Piancatelli et al., "A Simple Conversion of 4-Substituted 5-Hydroxy-3-oxocyclopentenes into the 2-Substituted Analogs", pp. 116–117 (1976).
Tetrahedron letters, Piancatelli et al., "A Useful Preparation of 4-Substituted 5-Hydroxy-3-oxocyclopentene", 39, pp. 3555–3558 (1976).
Amgew Chem., Seebach et al., 4-Hydroxy-2-cyclopenten-1-one aus Ketonen und 3-Nitropropionylchlorid, E ine eintache Methode zum Aufbau von Funfrangen, 89, pp. 334–335 (1977).
Tetrahedron Letters, Piancatelli et al., "A Useful Preparation of (±) T-Butyl 3-Hydroxy-5-Oxo-1-Cyclopentene-Heptanoate and Its 3-Deoxy-Derivative, Important Prostaglandin Intermediates," 13, pp. 1131–1134 (1977).
Tetrahedron, Piancatelli et al., "A New Synthesis of 3-Oxocyclopentenes," 34, pp. 2775–2778, (1978).
J. Org. Chem., Floyd, "Prestaglandins and Congeners". 18. Synthesis of Cyclopentenalone, Precurosors to Prostaglandins from 2-5-Oihyoro-2, 5-dimethoxyfurons, 43, pp. 1641–1643 (1978).
Tetrahedron, Piancatelli et al., "General Route and Mechanism Of The Rearrangement Of The 4-Substituted 5-Hydroxy-3-Oxocyclopentenes Into The 2-Substituted Analogs", 35, pp. 135–138. (1979).
Piancatelli et al., Tetrahedron, vol. 36, pp. 661–663, (1980).

*Primary Examiner*—Natalie Trousof
*Assistant Examiner*—James H. Reamer
*Attorney, Agent, or Firm*—Birch, Stewart, Kolasch & Birch

[57] ABSTRACT

A process for preparing cyclopentenolones in good yields which comprises treating a 4-hydroxy-4-$R_2$-5-$R_1$-2-cyclopentenone of the formula:

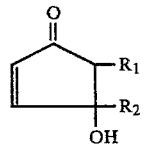

wherein $R_1$ is an alkyl group having not more than 6 carbon atoms, an alkenyl group having not more than 6 carbon atoms, an alkynyl group having not more than 6 carbon atoms or a group of the formula:

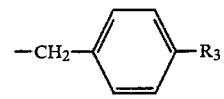

(in which $R_3$ is hydrogen, methyl or halogen) and $R_2$ is a hydrogen atom or a methyl group, provided that when $R_2$ is hydrogen, $R_1$ is neither α-methylallyl nor α-methylpropargyl, in an aqueous medium in the presence or absence of a metal salt at a temperature of 20° to 200° C. to give the corresponding 2-$R_1$-3-$R_2$-4-hydroxy-2-cyclopentenone of the formula:

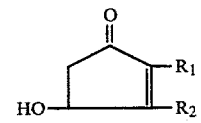

wherein $R_1$ and $R_2$ are each as defined above.

4 Claims, 3 Drawing Figures

PROCESS FOR PREPARING CYCLOPENTENOLONES

The present invention relates to a process for preparing cyclopentenolones. More particularly, it relates to a novel and improved process for preparing 2-$R_1$-3-$R_2$-4-hydroxy-2-cyclopentenones of the formula:

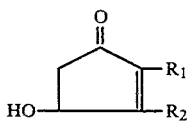
(I)

wherein $R_1$ is an alkyl group having not more than 6 carbon atoms, an alkenyl group having not more than 6 carbon atoms, an alkynyl group having not more than 6 carbon atoms or a group of the formula:

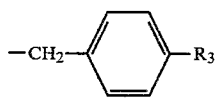

(in which $R_3$ is hydrogen, methyl or halogen) and $R_2$ is a hydrogen atom or a methyl group, provided that when $R_2$ is hydrogen, $R_1$ is neither α-methylallyl nor α-methylpropargyl.

In the above significances, the terms "alkyl", "alkenyl" and "alkynyl" are intended to mean straight, branched and cyclic moieties, inclusively. Specific examples thereof are methyl, ethyl, n-propyl, isopropyl, n-butyl, isobutyl, sec-butyl, n-pentyl, n-hexyl, allyl, α-methylallyl, α-ethylallyl, 4-pentenyl, propargyl, α-methylpropargyl, cyclopentyl, cyclohexyl, 2-cyclopentenyl, 2-cyclohexenyl, etc. The term "halogen" is intended to mean chlorine, bromine, fluorine, etc.

The 2-$R_1$-3-$R_2$-4-hydroxy-2-cyclopentenones (I) are useful as the alcoholic components of agricultural chemicals such as allethrines. For their production, various methods are known, some of which have been industrially adopted. But, they are still not satisfactory in respect of the yield, the complexity of operations, the problems of environmental pollution, etc.

For preparation of the 2-$R_1$-3-$R_2$-4-hydroxy-2-cyclopentenones (I), there are known two procedures starting from the corresponding 4-hydroxy-4-$R_2$-5-$R_1$-2-cyclopentenones of the formula:

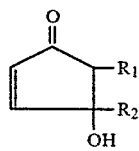
(II)

wherein $R_1$ and $R_2$ are each as defined above, of which the one comprises treating the 4-hydroxy-4-$R_2$-5-$R_1$-2-cyclopentenones (II) with basic alumina in a solvent mixture of benzene and ether [G. Piancatelli et al.: Tetrahedron, 34, 2775 (1978)] and the other comprises treating the 4-hydroxy-4-$R_2$-5-$R_1$-2-cyclopentenones (II) with 5% sodium hydrogen carbonate [Japanese Patent Publication (unexamined) No. 21146/78]. However, the former procedure is economically disadvantageous in requiring a large amount of expensive alumina. The latter procedure necessitates strong agitation for uniform dispersion of the 4-hydroxy-4-$R_2$-5-$R_1$-2-cyclopentenones (II) into the sodium hydrogen carbonate solution and is not satisfactory in the yield of the objective 2-$R_1$-3-$R_2$-4-hydroxy-2-cyclopentenones (I).

On the other hand, it is known that treatment of a prostaglandin intermediate of the formula:

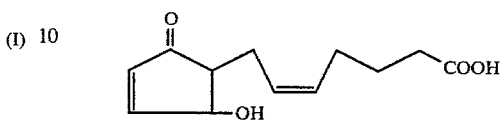

with 1 N sulfuric acid in a solvent mixture of water and dioxane affords a prostaglandin of the formula:

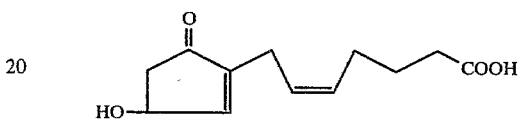

[M. B. Floyd, J. Org. Chem., 43, 1641 (1978)]. When the reaction conditions in this treatment are applied to the conversion of the 4-hydroxy-4-$R_2$-5-$R_1$-2-cyclopentenones (II) into the 2-$R_1$-3-$R_2$-4-hydroxy-2-cyclopentenones (I), there are by-produced various undesired substances, and the yield of the objective 2-$R_1$-3-$R_2$-4-hydroxy-2-cyclopentenones (I) is extremely lowered.

As the result of an extensive study, it has now been found that treatment of the 4-hydroxy-4-$R_2$-5-$R_1$-2-cyclopentenones (II) in an aqueous medium affords readily the corresponding 2-$R_1$-3-$R_2$-4-hydroxy-2-cyclopentenones (I) in a good yield.

According to the present invention, there is provided a process for preparing the 2-$R_1$-3-$R_2$-4-hydroxy-2-cyclopentenones (I) in a good yield within a short period of time which comprises treatment of the corresponding 4-hydroxy-4-$R_2$-5-$R_1$-2-cyclopentenones (II) in an aqueous medium.

The aqueous medium may be constituted with water alone or containing a small amount of any water-miscible or water-immiscible organic solvent (e.g. acetone, tetrahydrofuran, dioxane, toluene, xylene, diisopropyl ether, benzene). The weight of the aqueous medium to the starting 4-hydroxy-4-$R_2$-5-$R_1$-2-cyclopentenone (II) may be ordinarily from 0.5 to 100 fold, preferably from 5 to 40 fold.

The treatment is usually effected at a temperature of about 20° to 200° C. In order to accelerate the reaction rate, however, the presence of a metal salt in the aqueous medium or the elevation of the temperature to about 120° to 200° C. is preferred. In other words, the conversion can be accomplished in a short period of time either in the presence of a metal salt even if the temperature is relatively low (e.g. 20° to 120° C.) or at a temperature of about 120° to 200° C. even if the metal salt is not present. The pH of the aqueous medium is generally favored to be neutral, and when the movement of the pH to an acidic side by addition of the metal salt is observed, it is preferred to maintain the pH around 7 by incorporation of an appropriate amount of a basic substance into the reaction system.

Examples of the metal salt are magnesium chloride, magnesium bromide, magnesium nitrate, magnesium sulfate, manganese chloride, zinc chloride, copper chloride, copper sulfate, cobalt acetate, cobalt chloride, etc.

The amount of the metal salt may be usually from 0.001 to 10 mol, preferably from 0.01 to 1 mol, to one mol of the 2-$R_1$-3-$R_2$-4-hydroxy-2-cyclopentenone (I).

The mechanism in the treatment of the present invention is still uncertain. However, it may be presumed that the mechanism is substantially the same as in the use of an acid catalyst for the conversion of the prostaglandin intermediate into prostaglandin but, different from the case of using an acid catalyst, the by-production of undesired substances probably resulting from the aldol condensation of the once produced 2-$R_1$-3-$R_2$-4-hydroxy-2-cyclopentenone (I) is markedly inhibited.

The starting 4-hydroxy-4-$R_2$-5-$R_1$-2-cyclopentenone (II) can be produced, for instance, by reacting a furfural of the formula:

wherein $R_2$ is as defined above with an organic metal halide of the formula:

$R_1MX$ wherein M is Mg, Zn or Al($\frac{2}{3}$), X is chlorine, bromine or iodine and $R_1$ is as defined above, the organic metal halide being obtainable by reacting a halide of the formula: $R_1X$ with Mg, Zn or Al, and heating the resultant furan compound of the formula:

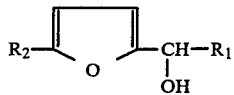

wherein $R_1$ and $R_2$ are each as defined above with water in the presence of a metal salt.

Alternatively, the 4-hydroxy-4-$R_2$-5-$R_1$-2-cyclopentenone (II) wherein $R_2$ is methyl is obtainable by the following method as disclosed in Japanese Patent Publication (unexamined) No. 21146/78:

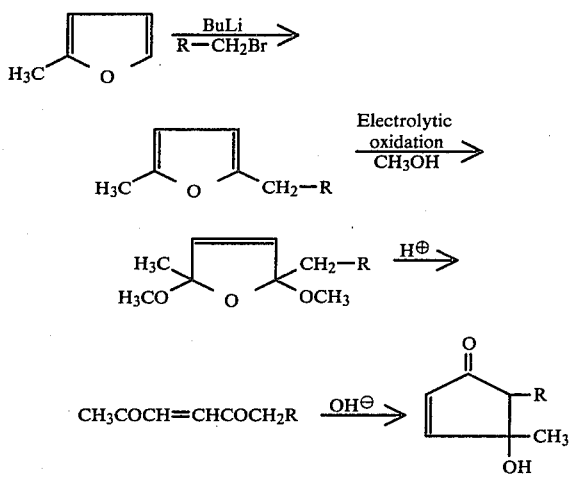

or by the following method as disclosed in G. Piancatelli et al.: Tetrahedron Letters, 39, 3555 (1976) and ibid., 34, 2775 (1978):

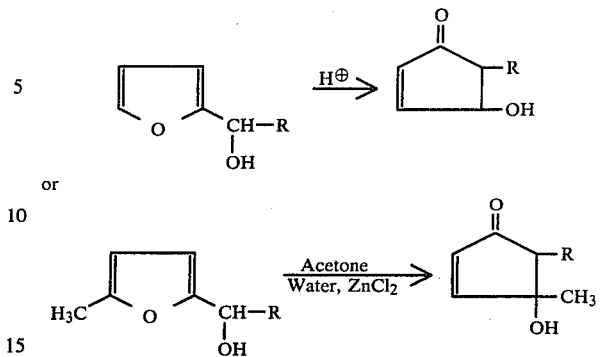

Practical and presently preferred embodiments of the present invention are illustratively shown in the following Examples.

EXAMPLE 1

Into a reaction vessel, a solution of 4-hydroxy-4-methyl-5-allyl-2-cyclopentenone (3 g) and $MgCl_2 \cdot 6H_2O$ (4.0 g) in water (120 ml) was charged, and the temperature was elevated up to 100° C. The contents were adjusted to pH 7.3 with 0.1 N NaOH solution, and stirring was continued at 100° C. for 4 hours, during which the pH was maintained at 7.0 to 7.3. After cooling, NaCl (40 g) was added to the reaction mixture, and the resultant mixture was extracted with ether (120 ml) 4 times. The extracts were combined together, dried over anhydrous magnesium sulfate and concentrated at 40° C. under reduced pressure to give an oily substance (2.7 g). The oily substance was chromatographed with silica gel (30 g), followed by development with a solvent mixture of ethyl acetate and hexane (1:2 by volume) to give 2-allyl-3-methyl-4-hydroxy-2-cyclopentenone (2.6 g). Yield, 87%. N.M.R. ($CDCl_3$, internal standard TMS, $\delta$ ppm, 90 MHz): 5.71 (complex m, 1H, —$CH_2$—C$\underline{H}$=$CH_aH_b$); 5.06 (m, 1H, —$CH_2$—CH=C$\underline{H}_aH_b$); 4.93 (m, 1H, —$CH_2$—CH=$CH_a\underline{H}_b$); 4.74 (broad d, 1H, 4-H); 3.94 (broad s, 1H, 4-O$\underline{H}$); 2.96 (d, 2H, —C$\underline{H}_2$—CH$CH_aH_b$); 2.85 (d of d, 1H, 5-H); 2.27 (d of d, 1H, 5-H); 2.11 (s, 3H, 3-C$\underline{H}_3$).

EXAMPLE 2

Into a reaction vessel, a solution of 4-hydroxy-4-methyl-5-propargyl-2-cyclopentenone (3 g) and $MgCl_2 \cdot 6H_2O$ (4.0 g) in water (120 ml) was charged, and the temperature was elevated up to 100° C. The contents were adjusted to pH 6.8 with 0.1 N NaOH solution, and stirring was continued at 100° C. for 4 hours, during which the pH was maintained at 6.8 to 7.0. After cooling, NaCl (40 g) was added to the reaction mixture and extracted with ether (120 ml) 4 times. The extracts were combined together, dried over anhydrous magnesium sulfate and concentrated at 40° C. under reduced pressure to give an oily substance (2.5 g). The oily substance was chromatographed with silica gel (30 g), followed by development with a solvent mixture of ethyl acetate and hexane (1:2 by volume) to give 2-propargyl-3-methyl-4-hydroxy-2-cyclopentenone (2.3 g). Yield, 77%. N.M.R. ($CDCl_3$, internal standard TMS, $\delta$ ppm, 90 MHz): 4.60 (broad d, 1H, 4-H); 3.95 (broad s, 1H, 4-O$\underline{H}$); 3.04 (d, 2H, —C$\underline{H}_2$—C≡H); 2.65 (d of d, 1H, 5-H); 2.38 (d of d, 1H, 5-H); 2.20 (s, 3H, 3-C$\underline{H}_3$); 1.98 (s, 1H, C≡C$\underline{H}$).

EXAMPLES 3 TO 18

In the same manner as in Example 1, the 4-hydroxy-4-$R_2$-5-$R_1$-2-cyclopentenone (II) (3 g) was treated to give the corresponding 2-$R_1$-3-$R_2$-4-hydroxy-2-cyclopentenone (I). The reaction conditions and the yields are shown in Table 1.

TABLE 1

| Example | 4-Hydroxy-4-$R_2$-5-$R_1$-2-cyclopentenone (II) | | Amount of $MgCl_2.6H_2O$ used (g) | pH | Yield of 2-$R_1$-3-$R_2$-4-hydroxy-2-cyclopentenone (I) |
|---|---|---|---|---|---|
| | $R_1$ | $R_2$ | | | |
| 3 | Methyl | Methyl | 4.8 | 6.8–7.1 | 88 |
| 4 | Propyl | Methyl | 4.0 | 6.5–7.1 | 83 |
| 5 | Hexyl | Methyl | 3.1 | 7.0–7.2 | 85 |
| 6 | Cyclohexyl | Methyl | 3.1 | 7.0–7.1 | 86 |
| 7 | 4-Pentenyl | Methyl | 3.4 | 6.5–7.1 | 90 |
| 8 | Benzyl | Methyl | 3.0 | 6.8–7.1 | 85 |
| 9 | p-Methylbenzyl | Methyl | 2.8 | 6.7–7.0 | 79 |
| 10 | p-Chlorobenzyl | Methyl | 2.6 | 6.8–7.4 | 81 |
| 11 | Methyl | Hydrogen | 4.5 | 6.9–7.2 | 87 |
| 12 | Propyl | Hydrogen | 4.5 | 6.8–7.3 | 85 |
| 13 | Hexyl | Hydrogen | 3.5 | 7.0–7.2 | 88 |
| 14 | Cyclohexyl | Hydrogen | 3.5 | 6.7–7.1 | 91 |
| 15 | 4-Pentenyl | Hydrogen | 3.5 | 7.0–7.3 | 92 |
| 16 | Benzyl | Hydrogen | 3.0 | 6.8–7.2 | 90 |
| 17 | p-Methylbenzyl | Hydrogen | 3.0 | 7.0–7.3 | 78 |
| 18 | p-Chlorobenzyl | Hydrogen | 3.0 | 6.6–7.0 | 83 |

EXAMPLE 19

Into a reaction vessel, a solution of 4-hydroxy-4-methyl-5-allyl-2-cyclopentenone (3 g) and $ZnCl_2$ (5 g) in water (120 ml) was charged, and the temperature was elevated up to 100° C. The contents were refluxed for 15 hours while stirring. After cooling, NaCl (40 g) was added to the reaction mixture, and the resulting mixture was extracted with toluene (120 ml) 4 times. The extracts were combined together and concentrated at 50° C. under reduced pressure to give an oily substance (2.5 g). The oily substance was chromatographed on silica gel (30 g), followed by development with a solvent mixture of ethyl acetate and hexane (1:2 by volume) to give 2-allyl-3-methyl-4-hydroxy-2cyclopentenone (2.4 g). Yield, 80%.

EXAMPLES 20 TO 23

In the same manner as in Example 19, 4-hydroxy-4-methyl-5-allyl-2-cyclopentenone (3 g) was treated to give 2-allyl-3-methyl-4-hydroxy-2-cyclopentenone. The reaction conditions and the yields are shown in Table 2.

TABLE 2

| Example | Metal salt used | Amount of metal salt used | Reaction time (hr) | Yield (%) |
|---|---|---|---|---|
| 20 | $MgCl_2.6H_2O$ | 10 | 50 | 70 |
| 21 | $CoCl_2.6H_2O$ | 5 | 40 | 72 |
| 22 | $CuCl_2.2H_2O$ | 10 | 24 | 69 |
| 23 | $CuSO_4$ | 10 | 24 | 65 |

EXAMPLE 24

In an autoclave, 4-hydroxy-4-methyl-5-allyl-2-cyclopentenone (20 g) and water (400 ml) were charged, and the resultant mixture was stirred at 180° C. for 6 hours in a nitrogen atmosphere. After cooling, sodium chloride (50 g) was added to the reaction mixture, and the resulting mixture was extracted with methyl isobutyl ketone. The extract was concentrated under reduced pressure to give 2-allyl-3-methyl-4-hydroxy-2-cyclopentenone (19 g). Yield, 95%. M.P. 130°–132° C./1.2 mmHg.

EXAMPLE 25

In an autoclave, 4-hydroxy-4-methyl-5-propargyl-2-cyclopentenone (3 g) and water (400 ml) were charged, and the resultant mixture was stirred at 150° C. for 6 hours in a nitrogen atmosphere. After cooling, sodium chloride (50 g) was added to the reaction mixture, the resulting mixture was extracted with ethyl acetate. The extract was concentrated under reduced pressure and purified on column chromatography to give 2-propargyl-3-methyl-4-hydroxy-2-cyclopentenone (2.7 g). Yield, 90% $n_D^{21}$ 1.5148.

EXAMPLES 26 TO 41

In the same manner as in Example 25, the 4-hydroxy-4-$R_2$-5-$R_1$-2-cyclopentenone (II) (3 g) was treated to give the corresponding 2-$R_1$-3-$R_2$-4-hydroxy-2-cyclopentenone (I). The reaction conditions and the yields are shown in Table 3.

TABLE 3

| Example | 4-Hydroxy-4-$R_2$-5-$R_1$-2-cyclopentenone (II) | | Reaction temperature (°C.) | Yield of 2-$R_1$-3-$R_2$-4-hydroxy-2-cyclopentenone (I) |
|---|---|---|---|---|
| | $R_1$ | $R_2$ | | |
| 26 | Methyl | Methyl | 180 | 90 |
| 27 | Propyl | Methyl | 180 | 85 |
| 28 | Hexyl | Methyl | 180 | 85 |
| 29 | Cyclohexyl | Methyl | 180 | 87 |
| 30 | 2-Cyclopentenyl | Methyl | 180 | 85 |
| 31 | 2-Cyclohexenyl | Methyl | 180 | 85 |
| 32 | α-Methylallyl | Methyl | 180 | 90 |
| 33 | α-Ethylallyl | Methyl | 180 | 89 |
| 34 | 4-Pentenyl | Methyl | 180 | 90 |
| 35 | α-Methylpropargyl | Methyl | 150 | 89 |
| 36 | Benzyl | Methyl | 180 | 86 |
| 37 | p-Methylbenzyl | Methyl | 180 | 80 |
| 38 | p-Chlorobenzyl | Methyl | 180 | 82 |
| 39 | Methyl | Hydrogen | 170 | 92 |
| 40 | Hexyl | Hydrogen | 170 | 88 |
| 41 | Benzyl | Hydrogen | 170 | 90 |

What is claimed is:

1. A process for preparing cyclopentenolones which comprises treating a 4-hydroxy-4-$R_2$-5-$R_1$-2-cyclopentenone of the formula:

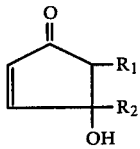

wherein $R_1$ is an alkyl group having not more than 6 carbon atoms, an alkenyl group having not more than 6 carbon atoms, an alkynyl group having not more than 6 carbon atoms or a group of the formula:

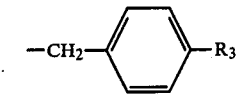

in which $R_3$ is hydrogen, methyl or halogen and $R_2$ is a hydrogen atom or a methyl group, provided that when $R_2$ is hydrogen, $R_1$ is neither α-methylallyl nor α-methylpropargyl, in an aqueous medium to give the corresponding 2-$R_1$-3-$R_2$-4-hydroxy-2-cyclopentenone of the formula:

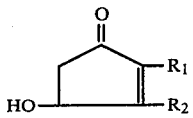

wherein $R_1$ and $R_2$ are each as defined above.

2. The process according to claim 1, wherein the treatment is carried out at a temperature of 20° to 200° C.

3. The process according to claim 1, wherein the treatment is carried out at a temperature of 120° to 200° C.

4. The process according to claim 1, wherein the treatment is carried out in the presence of a metal salt.

* * * * *

UNITED STATES PATENT AND TRADEMARK OFFICE
CERTIFICATE OF CORRECTION

PATENT NO. : 4,347,386

DATED : August 31, 1982

INVENTOR(S) : Kenji Saito etal.

It is certified that error appears in the above-identified patent and that said Letters Patent is hereby corrected as shown below:

Delete the three (3) pages of drawings from Patent No. 4,347,386.

On The Title Page, "3 Drawing Figures" should read

-- No Drawings --.

Signed and Sealed this

Sixteenth Day of August 1983

[SEAL]

Attest:

GERALD J. MOSSINGHOFF

Attesting Officer     Commissioner of Patents and Trademarks